United States Patent
Shin et al.

(10) Patent No.: US 8,652,830 B2
(45) Date of Patent: Feb. 18, 2014

(54) APPARATUS FOR STIMULATING CELL

(75) Inventors: Jennifer H. Shin, Daejeon (KR); SunHee Kim, Daejeon (KR); Jin Young Park, Daejeon (KR); Yang-Hann Kim, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 904 days.

(21) Appl. No.: 12/700,356

(22) Filed: Feb. 4, 2010

(65) Prior Publication Data

US 2011/0136215 A1    Jun. 9, 2011

(30) Foreign Application Priority Data

Dec. 4, 2009   (KR) .................. 10-2009-0120156

(51) Int. Cl.
*C12M 1/36* (2006.01)
*B01F 11/02* (2006.01)

(52) U.S. Cl.
USPC ............... 435/286.7; 435/303.3; 366/114; 366/127

(58) Field of Classification Search
USPC .......... 435/173.7, 173.8, 286.1, 286.7, 303.3; 366/127, 114
See application file for complete search history.

(56) References Cited

U.S. PATENT DOCUMENTS

| | | | | |
|---|---|---|---|---|
| 4,894,342 A | * | 1/1990 | Guinn et al. | ............... 435/297.4 |
| 2001/0021529 A1 | | 9/2001 | Takagi | |
| 2002/0009015 A1 | * | 1/2002 | Laugharn et al. | ............. 366/108 |
| 2007/0299539 A1 | | 12/2007 | Othman et al. | |
| 2008/0021327 A1 | | 1/2008 | El-Bialy et al. | |

FOREIGN PATENT DOCUMENTS

| | | |
|---|---|---|
| JP | 2005-160340 A | 6/2005 |
| KR | 2003-0032925 A | 4/2003 |

OTHER PUBLICATIONS

Korean Office Action of the corresponding Korean Application No. 10-2009-0120156, dated Jul. 22, 2011.
Tsai, Wen-Chung at al., "Therapeutic Ultrasound Stimulation of Tendon Cell Migration," Connective Tissue Research, 49-5, 367-373, (2008).

* cited by examiner

*Primary Examiner* — William H Beisner
(74) *Attorney, Agent, or Firm* — Global IP Counselors, LLP (57) ABSTRACT

An apparatus for stimulating cell includes a cell culture chamber, a control device, and first and second exciters. The cell culture chamber includes cell and culture medium. The control device receives first and second exciting signals, and controls magnitudes and phases of the received first and second exciting signals so that a sound pressure level in a focused zone is higher than a sound pressure level in a zone other than the focused zone, and outputs first and second controlled exciting signals. The first and second exciters receive the first and second controlled exciting signals and excite the cell culture chamber.

6 Claims, 4 Drawing Sheets

APPARATUS FOR STIMULATING CELL

CROSS-REFERENCE TO RELATED APPLICATIONS

This U.S. National stage application claims priority under 35 U.S.C. §119(a) to Korean Patent Application No. 10-2009-0120156, filed in the Republic of Korea on Dec. 4, 2009, the entire contents of which are hereby incorporated herein by reference.

BACKGROUND OF THE INVENTION

1. Field of the Invention

The present invention relates to an apparatus for stimulating cell.

2. Background Information

Recently, a concern about various medical effect of an ultrasound is centralized in the medical field. Also, many results of clinical studies referring to this medical effect are being published, accordingly a medical treatment device is being developed. But, an effect of the ultrasound on a cell has not been studied accurately. Accordingly, the study for interpreting an accurate mechanism about the effect of the ultrasound on the cell is being done, and in this endeavor, various ultrasound stimulators which stimulates on the cell are being developed.

The ultrasound cell stimulators being used recently can be categorized into three groups.

One is an apparatus which stimulates cells by using the commercialized ultrasound stimulator attached on a cell culture chamber in which cells are grown [Liang-Wei Chieh, Therapeutic Ultrasound Stimulation of Tendon Cell Migration, Connective tissue research, 2008; 49 (5):367-73].

Another is an apparatus which stimulates cells by using the ultrasound stimulator attached on a floor surface of the cell culture chamber, as like a cell stimulator described in Ultrasound accelerated tissue engineering process [US Patent Publication No. US20070299539A1]. To transmit an ultrasound wave uniformly by this apparatus is easier than to transmit an ultrasound wave uniformly by the apparatus of Liang-Wei Chieh. This apparatus has a merit to control the magnitude of the transmitted ultrasound wave.

However, since the ultrasound stimulator is attached on the floor surface of the cell culture chamber, there is a problem that it is not easy to observe the cell by microscope. Also, since devices for maintaining a temperature of cell culture medium and $CO_2$ concentration are installed in the apparatus, there is a problem that it is not easy to observe the cell by microscope, because the cell is shaded by the devices.

The other is an apparatus which stimulates cells by using the ultrasound stimulator which has a needle shape and is inserted in the cell culture chamber. According to this apparatus, it is able to observe the cell by the microscope. However, in this case, there is a problem that it is difficult to control the magnitude of the cell stimulation accurately or to stimulate the cell at a constant magnitude successively because of using a point source.

SUMMARY OF THE INVENTION

The present invention is conceived to solve the aforementioned problems. Accordingly, the present invention provides an apparatus for stimulating cell, by which the ultrasound stimulation can be excited only to the selected focused zone compared to a conventional apparatus for stimulating cell by which it is difficult to stimulate an only desired part using one ultrasound exciter or to stimulate uniformly as a whole, by locating a plurality of the ultrasound exciters outside the cell culture chamber and controlling the exciting signals inputted to the plurality of the ultrasound exciters so that the sound pressure level in the focused zone is higher than the sound pressure level in the zone other than the focused zone.

The present invention also provides an apparatus for stimulating cell, in which a mutual reaction between the cell excited and the cell not excited can be observed by the microscope in real time by locating the plurality of the ultrasound exciters outside the cell culture chamber and locating the transparent substrate in the upper side and the lower side of the cell culture chamber respectively.

The present invention also provides an apparatus for stimulating cell, in which a reaction of the cell generated as stimulating cell in the cell culture chamber can be observed well by the microscope without being shaded by the devices by locating devices for maintaining a temperature of the cell culture medium and a concentration of $CO_2$ outside the cell culture chamber.

An apparatus for stimulating cell related to a first aspect includes: a cell culture chamber for including cell and culture medium; a control device for receiving first and second exciting signals, controlling magnitudes and phases of the received first and second exciting signals so that a sound pressure level in a focused zone is higher than a sound pressure level in a zone other than the focused zone and outputting first and second controlled exciting signals; first and second exciters for receiving the first and second controlled exciting signals and exciting the cell culture chamber.

Consequently, according to the apparatus for stimulating cell related to the first aspect, since the cell culture chamber is excited by the first and second controlled exciting signals whose magnitudes and phases are controlled so that the sound pressure level in the focused zone is higher than the sound pressure level in the zone other than the focused zone, the focused zone to which the ultrasound stimulation is excited can be selected, and the ultrasound stimulation can be excited only to the selected focused zone.

An apparatus for stimulating cell related to a second aspect is the apparatus for stimulating cell related to the first aspect, wherein the apparatus for stimulating cell further includes a transparent substrate located in the upper side and the lower side of the cell culture chamber.

Consequently, according to the apparatus for stimulating cell related to the second aspect, since the transparent substrate is located in the upper side and the lower side of the cell culture chamber, an inner side of the cell culture chamber can be observed by the microscope.

An apparatus for stimulating cell related to a third aspect is the apparatus for stimulating cell related to the second aspect, wherein the apparatus for stimulating cell further includes an outer chamber surrounding the cell culture chamber, wherein the first and second exciters are installed on the inner wall of the outer chamber.

Consequently, according to the apparatus for stimulating cell related to the second aspect, since the transparent substrate is located in the upper side and the lower side of the cell culture chamber, also the first and second exciters are installed on the inner wall of the outer chamber, it can be removed that exciters shade the upper side and the lower side of the cell culture chamber and a reaction of the cell generated as stimulating the cell in the cell culture chamber can be observed well by the microscope.

An apparatus for stimulating cell related to a fourth aspect is the apparatus for stimulating cell related to the third aspect, wherein an impedance matching fluid is filled in the outer chamber.

Consequently, according to the apparatus for stimulating cell related to the fourth aspect, since the impedance matching fluid is filled in the outer chamber, the ultrasound stimulation from the first and second exciters can be maintained uniformly by a gel type of the impedance fluid, and the ultrasound stimulation can be transmitted to the cell culture chamber as it is without a loss generated by a change of an impedance according to a change of medium (exciters-impedance matching fluid-cell).

An apparatus for stimulating cell related to a fifth aspect is the apparatus for stimulating cell related to any one of the first to fourth aspects, wherein the apparatus for stimulating cell further includes a water bath for controlling a temperature of the culture medium, which is connected to the cell culture chamber, wherein the water bath includes a humidifier and a culture medium buffer connected between the humidifier and the cell culture chamber.

Consequently, according to the apparatus for stimulating cell related to the fifth aspect, since the water bath is connected to the cell culture chamber, and the culture medium filled in the water bath is supplied to the inner side of the cell culture chamber, a temperature of the culture medium of the cell culture chamber can be controlled suitably by supplying the culture medium whose temperature is maintained constantly to the inner side of the cell culture chamber.

An apparatus for stimulating cell related to a sixth aspect is the apparatus for stimulating cell related to the fifth aspect, wherein a CO2 supply device for controlling a CO2 concentration in the cell culture chamber, which is connected to the cell culture chamber through the water bath.

Consequently, according to the apparatus for stimulating cell related to the sixth aspect, since the CO2 supply device is connected to the cell culture chamber through the water bath, a CO2 concentration of the inner side of the cell culture chamber can be maintained by supplying CO2 to the inner side of the cell culture chamber successively.

An apparatus for stimulating cell related to a seventh aspect includes: a cell culture chamber for including cell and culture medium; a control device for receiving first and second exciting signals, controlling magnitudes and phases of the received first and second exciting signals so that a contrast between spatially averaged control energy in a focused zone and sum of energies of the first and second exciting signals is maximized and outputting first and second controlled exciting signals; first and second exciters for receiving the first and second controlled exciting signals and exciting the cell culture chamber.

Consequently, according to the apparatus for stimulating cell related to the seventh aspect, since the cell culture chamber is excited by the first and second controlled exciting signals whose magnitudes and phases are controlled so that a contrast between spatially averaged control energy in a focused zone and sum of energies of the first and second exciting signals is maximized, the focused zone to which the ultrasound stimulation is excited can be selected, and the ultrasound stimulation can be excited only to the selected focused zone.

An apparatus for stimulating cell related to an eighth aspect includes: a cell culture chamber for including cell and culture medium; a control device for receiving first and second exciting signals, controlling magnitudes and phases of the received first and second exciting signals so that a contrast between spatially averaged control energy in a pre-determined zone and spatially averaged control energy in a zone other than the focused zone is maximized and outputting first and second controlled exciting signals; first and second exciters for receiving the first and second controlled exciting signals and exciting the cell culture chamber.

Consequently, according to the apparatus for stimulating cell related to the eighth aspect, since the cell culture chamber is excited by the first and second controlled exciting signals whose magnitudes and phases are controlled so that a contrast between spatially averaged control energy in a pre-determined zone and spatially averaged control energy in a zone other than the focused zone is maximized, the focused zone to which the ultrasound stimulation is excited can be selected, and the ultrasound stimulation can be excited only to the selected focused zone.

An apparatus for stimulating cell related to a ninth aspect includes: a cell culture chamber for including cell and culture medium; a control device for receiving first and second exciting signals, controlling magnitudes and phases of the received first and second exciting signals so that a contrast between spatially averaged control energy in a pre-determined zone and spatially averaged control energy in total zone that includes the focused zone and a zone other than the focused zone is maximized and outputting first and second controlled exciting signals; first and second exciters for receiving the first and second controlled exciting signals and exciting the cell culture chamber.

Consequently, according to the apparatus for stimulating cell related to the ninth aspect, since the cell culture chamber is excited by the first and second controlled exciting signals whose magnitudes and phases are controlled so that a contrast between spatially averaged control energy in a pre-determined zone and spatially averaged control energy in total zone that includes the focused zone and a zone other than the focused zone is maximized, the focused zone to which the ultrasound stimulation is excited can be selected, and the ultrasound stimulation can be excited only to the selected focused zone.

According to the present invention configured as described above, since a plurality of the ultrasound exciters are located outside the cell culture chamber and the exciting signals inputted to the plurality of the ultrasound exciters is controlled so that the sound pressure level in the focused zone is higher than the sound pressure level in the zone other than the focused zone, the focused zone to which the ultrasound stimulation is excited can be selected, and the ultrasound stimulation can be excited only to the selected focused zone compared to a conventional apparatus for stimulating cell by which it is difficult to stimulate an only desired part using one ultrasound exciter or to stimulate uniformly as a whole.

According to the present invention, since the plurality of the ultrasound exciters are located outside the cell culture chamber and the transparent substrate is located in the upper side and the lower side of the cell culture chamber respectively, a mutual reaction between the cell excited and the cell not excited can be observed by the microscope in real time.

Also, according to the present invention, since devices for maintaining a temperature of the cell culture medium and a concentration of CO2 are located outside the cell culture chamber, a reaction of the cell generated as stimulating the cell in the cell culture chamber can be observed well by the microscope without being shaded by the devices.

The objects, constructions and effects of the present invention are included in the following embodiments and drawings. The advantages, features, and achieving methods of the present invention will be more apparent from the following detailed description in conjunction with embodiments and the accompanying drawings. The same reference numerals are used throughout the drawings to refer to the same or like parts.

BRIEF DESCRIPTION OF THE DRAWINGS

The above and other features and advantages of the present invention will become more apparent to those of ordinary skill in the art by describing in detail preferred embodiments thereof with reference to the attached drawings, in which.

DETAILED DESCRIPTION OF THE PREFERRED EMBODIMENTS

Above all, a theoretical background relating to the present invention is described in detail.

Figure 1:
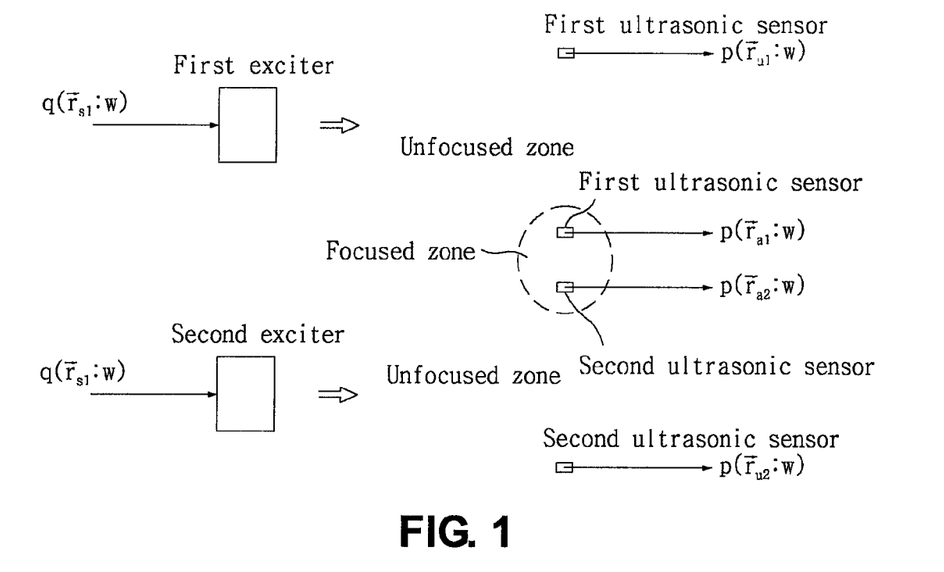
FIG. 1 is a schematic drawing for explaining the theoretical contents relating to the present invention.

FIG. 1 is a schematic drawing for explaining the theoretical contents relating to the present invention. FIG. 1 shows a control space schematically. In the control space, the first exciter and the second exciter are installed. The control space is divided into a zone that is selected as a focused zone, where the ultrasound stimulation is excited (hereinafter, it is called as the "focused zone"), and a zone other than the focused zone, where the ultrasound stimulation is not excited (hereinafter, it is called as the "unfocused zone"). In FIG. 1, the focused zone and unfocused zone are schematically distinguished by a circular dotted line. The unfocused zone means practically the total zone other than the zone where the cell is located.

In the case that there are the first exciter to the Nth exciter in the control space, the sound pressure ($p(\vec{r}_j|r_{s,i};\omega)$, the signal which is sensed by an ultrasonic sensor) at arbitrary position ($\vec{r}_j$, the position where the ultrasonic sensor is installed) within the control space, which is generated by the first exciter to the Nth exciter can be written as the following Equation 1.

$$p(\vec{r}_j|\vec{r}_{s,i};\omega) = \sum_{i=1}^{n} G(\vec{r}_j|\vec{r}_{s,i};\omega)q(\vec{r}_{s,i};\omega) \quad \text{Equation 1}$$

Here, $q(\vec{r}_{s,i};\omega)$ is the signal which is inputted to the ith exciter which is located at the position of $\vec{r}_{s,i}$ and $G(\vec{r}_j|r_{s,i};\omega)$ and is a transfer function which represents the relation between $q(\vec{r}_{s,i};\omega)$ and $(p(\vec{r}_j|r_{s,i};\omega)$.

In the case of two exciters and two positions, the Equation 1 can be written as the following Equation 2 in matrix form.

$$\begin{bmatrix} p(\vec{r}_1;\omega) \\ p(\vec{r}_2;\omega) \end{bmatrix} = \begin{bmatrix} G(\vec{r}_1|\vec{r}_{s1};\omega) & G(\vec{r}_1|\vec{r}_{s2};\omega) \\ G(\vec{r}_2|\vec{r}_{s1};\omega) & G(\vec{r}_2|\vec{r}_{s2};\omega) \end{bmatrix} \begin{bmatrix} q(\vec{r}_{s1};\omega) \\ q(\vec{r}_{s2};\omega) \end{bmatrix} \quad \text{Equation 2}$$

$$p = Gq$$

As shown in FIG. 1, in the case that the exciters are two (that is, i=1, 2), the positions in which the ultrasonic sensors are installed are two in the focused zone (that is, j=1, 2) and two in the unfocused zone, the matrix expressions are like the following Equation 3 and 4. In the Equation 3 and 4, the below subscripts a and u stand for the focused zone and the unfocused zone respectively.

$$\begin{bmatrix} p(\vec{r}_{a1};\omega) \\ p(\vec{r}_{a2};\omega) \end{bmatrix} = \begin{bmatrix} G(\vec{r}_{a1}|\vec{r}_{s1};\omega) & G(\vec{r}_{a1}|\vec{r}_{s2};\omega) \\ G(\vec{r}_{a2}|\vec{r}_{s1};\omega) & G(\vec{r}_{a2}|\vec{r}_{s2};\omega) \end{bmatrix} \begin{bmatrix} q(\vec{r}_{s1};\omega) \\ q(\vec{r}_{s2};\omega) \end{bmatrix} \quad \text{Equation 3}$$

$$p_a = G_a q$$

$$\begin{bmatrix} p(\vec{r}_{u1};\omega) \\ p(\vec{r}_{u2};\omega) \end{bmatrix} = \begin{bmatrix} G(\vec{r}_{u1}|\vec{r}_{s1};\omega) & G(\vec{r}_{u1}|\vec{r}_{s2};\omega) \\ G(\vec{r}_{u2}|\vec{r}_{s1};\omega) & G(\vec{r}_{u2}|\vec{r}_{s2};\omega) \end{bmatrix} \begin{bmatrix} q(\vec{r}_{s1};\omega) \\ q(\vec{r}_{s2};\omega) \end{bmatrix} \quad \text{Equation 4}$$

$$p_u = G_u q$$

The matrix expression about the control space that includes all of the focused zone and the unfocused zone (hereinafter, it is called the "total zone") is like Equation 5. In the Equation 5, the below subscript t stands for the total zone.

$$\begin{bmatrix} p(\vec{r}_{a1};\omega) \\ p(\vec{r}_{a2};\omega) \\ p(\vec{r}_{u1};\omega) \\ p(\vec{r}_{u2};\omega) \end{bmatrix} = \begin{bmatrix} G(\vec{r}_{a1}|\vec{r}_{s1};\omega) & G(\vec{r}_{a1}|\vec{r}_{s2};\omega) \\ G(\vec{r}_{a2}|\vec{r}_{s1};\omega) & G(\vec{r}_{a2}|\vec{r}_{s2};\omega) \\ G(\vec{r}_{u1}|\vec{r}_{s1};\omega) & G(\vec{r}_{u1}|\vec{r}_{s2};\omega) \\ G(\vec{r}_{u2}|\vec{r}_{s1};\omega) & G(\vec{r}_{u2}|\vec{r}_{s2};\omega) \end{bmatrix} \begin{bmatrix} q(\vec{r}_{s1};\omega) \\ q(\vec{r}_{s2};\omega) \end{bmatrix} \quad \text{Equation 5}$$

$$p_t = G_t q$$

And then, a representative physical quantity showing control characteristics in an arbitrary zone must be defined. In the present invention, the physical quantity is defined as spatially averaged control energy and this can be written as the following Equation 6.

$$e = \frac{1}{2}p^*p = q^H\left(\frac{1}{2}G^H G\right)q = q^H R q \quad \text{Equation 6}$$

(* is the conjugate operator.)

The reason that the representative physical quantity showing control characteristics in an arbitrary zone is defined as spatially averaged control energy is because it is not enough to show spatial control characteristics in an arbitrary zone with only sound pressure level at each position. Therefore, in the present invention, the spatially averaged control energy of the focused zone, the spatially averaged control energy of the unfocused zone, and the spatially averaged control energy of the total zone are considered as the sound pressure level in each zone.

In the Equation 6, matrix R is the correlation matrix representing a degree of interference that each exciter makes in an arbitrary zone and the number 2 represents the number of the positions in which ultrasonic sensors are installed in a certain zone. For easy understanding, the Equation 6 corresponds to the simple case that the number of the positions is 2, but this can be changed by the number of the positions that ultrasonic sensors are installed in an arbitrary zone.

On the basis of the Equation 6, each spatially averaged control energy, that is sound pressure level of the focused zone, the unfocused zone, and the total zone can be written as the following Equations 7, 8, and 9 respectively.

$$e_a = q^H R_a q \quad \text{Equation 7}$$

$$e_u = q^H R_u q \quad \text{Equation 8}$$

$$e_t = q^H R_t q \quad \text{Equation 9}$$

Hereafter, how to determine the first controlled exciting signal and the second controlled exciting signal, which are necessary to generate the focused zone and the unfocused zone in control space, using Equations 7, 8, and 9, which correspond to the sound pressure levels of focused zone, unfocused zone, and total zone, will be described.

There are three kinds of methods. The first method is to determine the controlled exciting signal by maximizing the contrast between the sound pressure level of the focused zone and the given total magnitude of input. The second method is to determine the controlled exciting signal by maximizing the contrast between the sound pressure level of the focused zone and the sound pressure level of the unfocused zone. The third method is to determine the controlled exciting signal by maximizing the contrast between the sound pressure level of the focused zone and the sound pressure level of the total zone.

1. Determination of controlled exciting signals for maximizing the contrast between sound pressure level of a focused zone and the given total magnitude of input The total magnitude of input is defined as the sum of a squared absolute value of a complex magnitude of the first exciting signal and a squared absolute value of a complex magnitude of the second exciting signal, and this can be called control effort. The total magnitude of input is written as the following Equation 10.

$$\text{total magnitude of input} = |G_0|^2 q^H q \quad \text{Equation 10}$$

Here, $|G_0|^2$ is a normalizing constant to match with the dimension of control energy.

The contrast between sound pressure level of the focused zone and total magnitude of input can be written as the following Equation 11 by using the Equation 7 and 10, and this is defined as "control brightness."

$$\alpha = \frac{q^H R_a q}{|G_0|^2 q^H q} \quad \text{Equation 11}$$

Accordingly, determining the controlled exciting signal for maximizing the contrast between the sound pressure level of the focused zone and total magnitude of input to obtain the eigenvector that maximizes the Rayleigh quotient α can be written as the following Equation 12.

$$R_b q = \alpha |G_0|^2 q \quad \text{Equation 12}$$

In this case, the eigenvectors corresponding to the maximum eigenvalue are the first controlled exciting signal and the second controlled exciting signal.

2. Determination of controlled source signals for maximizing the contrast between the sound pressure level of the focused zone and the sound pressure level of the unfocused zone The contrast between the sound pressure level of the focused zone and the sound pressure level of the unfocused zone can be written as the following Equation 13 by using the Equations 7 and 8, and this is defined as "control contrast 1."

$$\beta = \frac{q^H R_a q}{q^H R_u q} \quad \text{Equation 13}$$

Accordingly, determining controlled exciting signals for maximizing the contrast between the sound pressure level of a focused zone and the sound pressure level of an unfocused zone to obtain the eigenvector which maximizes the Rayleigh quotient β can be written as the following Equation 14.

$$R_u^{-1} R_a q = \beta q \quad \text{Equation 14}$$

In this case, the eigenvectors corresponding to maximum eigenvalues are the first controlled exciting signal and the second controlled exciting signal.

3. Determination of controlled exciting signals for maximizing the contrast between the sound pressure level of the focused zone and the sound pressure level of the total zone.

The contrast between the sound pressure level of the focused zone and the sound pressure level of the total zone can be written as the following Equation 15 by using the Equations 7 and 9, and this is defined as "control contrast 2."

$$\gamma = \frac{q^H R_a q}{q^H R_t q} \quad \text{Equation 15}$$

Accordingly, determining controlled exciting signals for maximizing the contrast between the sound pressure level of the focused zone and the sound pressure level of the total zone to obtain the eigenvector which maximizes the Rayleigh quotient γ can be written as the following Equation 16.

$$R_t^{-1} R_a q = \gamma q \quad \text{Equation 16}$$

In this case, the eigenvectors corresponding to the maximum eigenvalue are the first controlled exciting signal and the second controlled exciting signal.

The methods related to the prior art have used the relation between the cell and the exciter restrictively, but the present invention uses the method to obtain the optimized exciting signal by measuring transfer functions.

So, the present invention, unlike the active control only reducing the sound pressure level at some designated positions, can enlarge the relative difference of the sound pressure level between zones within control space. That is, the present invention performs control to enlarge not only the magnitude of the sound pressure level corresponding to control brightness but also the control contrast between two zones being different from each other.

Figure 2:
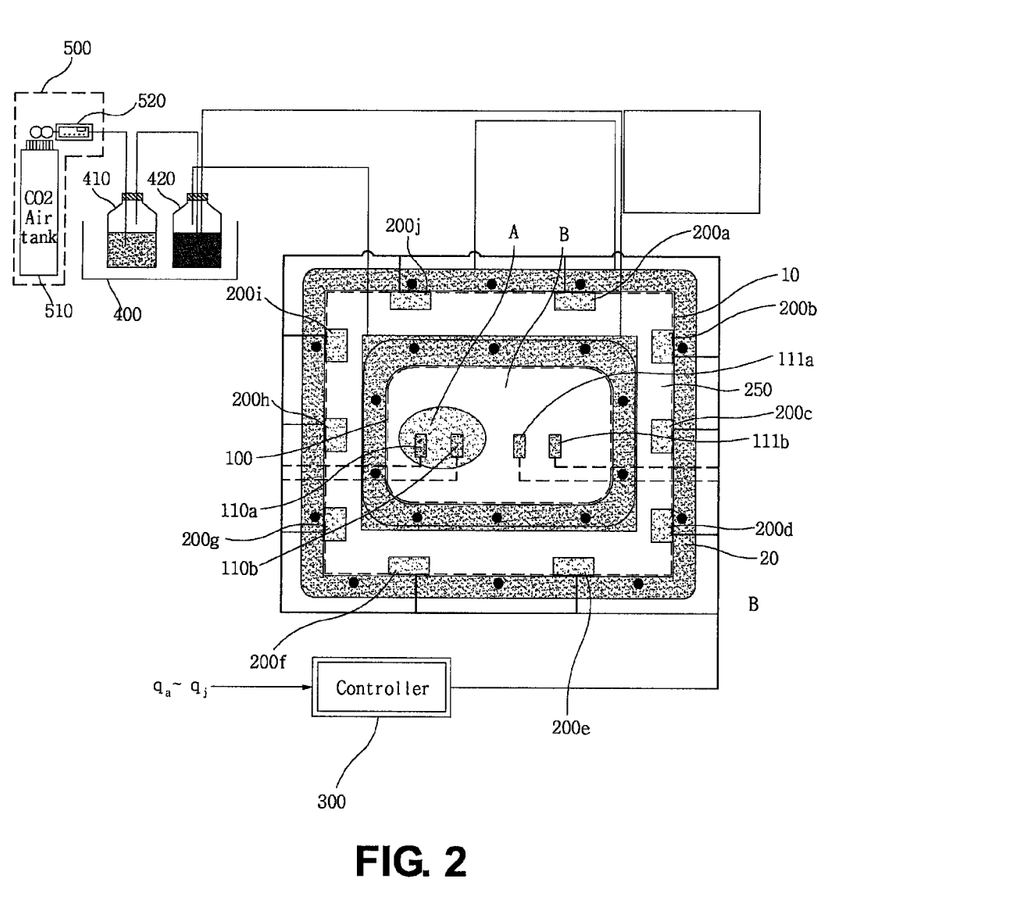
FIG. 2 is a schematic drawing describing the structure of the apparatus for stimulating cell according to an embodiment of the present invention.
Figure 3:
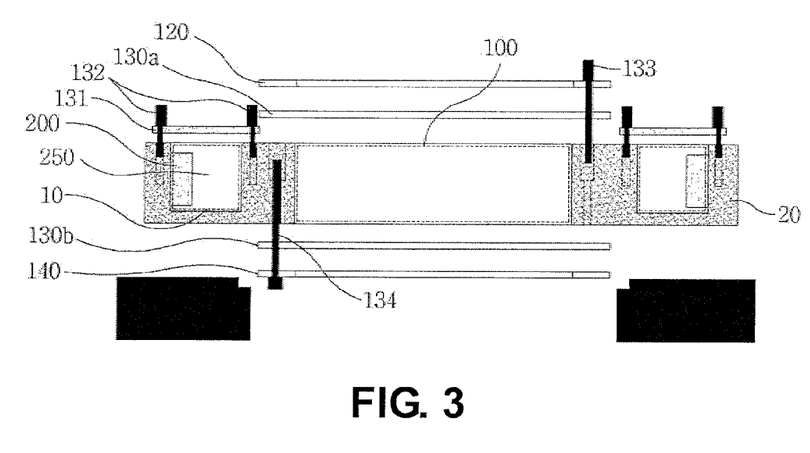
FIG. 3 is a cross sectional drawing describing the structure of the apparatus for stimulating cell according to an embodiment of the present invention.

FIG. 2 is a schematic drawing describing the structure of the apparatus for stimulating cell according to an embodiment of the present invention, and FIG. 3 is a cross sectional drawing describing the structure of the apparatus for stimulating cell according to an embodiment of the present invention.

As showed in FIG. 2 and FIG. 3, the apparatus for stimulating cell according to an embodiment of the present invention comprises a cell culture chamber 100, a controller 300, a plurality of ultrasound stimulators 200a to 200j. Also, the apparatus for stimulating cell according to an embodiment of the present invention comprises an outer chamber 10 surrounding the cell culture chamber 100, an upper transparent substrate 130a and a lower transparent substrate 130b are located respectively in the upper side and the lower side of the cell culture chamber 100. An impedance matching fluid 250 is filled in the outer chamber 10. Also, the apparatus for stimulating cell according to an embodiment of the present invention further comprises a water bath 400 connected to the cell culture chamber 100, a CO2 supply device 500 connected to the cell culture chamber 100 through the water bath 400. Meanwhile, as showed in FIG. 2 and FIG. 3, the cell culture chamber 100 which has a control space (a focused zone (A) and an unfocused zone (B)) in which an ultrasound stimulation is controlled and the outer chamber 10 which has a space in which the impedance matching fluid is filled are installed in a frame 20. The frame 20 can be formed by Aluminium (Al).

The cell culture chamber 100 includes the cell and the culture medium on the inside. The cell culture chamber 100 is attachable or separable on the microscope and is surrounded with the outer chamber 10. The inside of the cell culture chamber 100 is formed such that the medium is inserted into the inside of the cell culture chamber 100 and the cell is cultured in the inside of the cell culture chamber 100.

The transparent substrates (referring to FIG. 3) formed of transparent material as like polycarbonate are located in the upper side and the lower side of the cell culture chamber 100 respectively. As described above, since the transparent substrates are located in the upper side and the lower side of the cell culture chamber 100 respectively, the inside of the cell culture chamber 100 can be observed through the microscope.

The outer chamber 10 surrounds the cell culture chamber 100. The plurality of the exciters 200a to 200j is installed on the inner wall of the outer chamber 10 surrounding the cell culture chamber 100.

The impedance matching fluid 250 is filled in the outer chamber 10. Concretely, the impedance matching fluid 250 is filled between the cell culture chamber 100 and the plurality of the exciters 200a to 200j. Since the impedance matching fluid 250, as a gel type of the material, maintains an environment which stimulates the cell of the cell culture chamber 100 by maintaining an impedance constantly, a condition for ultrasound mapping can be maintained. Consequently, according to the apparatus for stimulating cell of the present invention, since the ultrasound stimulation from the plurality of the exciters 200a to 200j is maintained uniformly, the ultrasound stimulation can be transmitted to the cell culture chamber 100 without a loss generated by a change of an impedance according to a change of medium (exciters-impedance matching fluid-cell).

Also, a water bath 400 includes a humidifier 410 and a culture medium buffer 420. The humidifier 410 is connected to the culture medium buffer 420. The culture medium buffer 420 is connected to the cell culture chamber 100 through a tube pump 430.

The humidifier 410 controls a humidity of CO2 gas supplied to the culture medium buffer 420. The culture medium buffer 420 has the culture medium in it. This culture medium is supplied to the inside of the cell culture chamber 100 by the tube pump 430. Like this, since the culture medium is supplied to the inside of the cell culture chamber 100 successively, a temperature of the culture medium of the cell culture chamber 100 can be maintained suitably. Also, like this, since the temperature of the culture medium is maintained suitably, the survival of the cell is maintained well for experimenting about the cell.

The CO2 supply device 500 is connected to the humidifier 410. The CO2 supply device 500 includes a CO2 Air tank 510 and a flow meter 520. The CO2 Air tank 510 stores the CO2 gas which has a predetermined concentration. The predetermined concentration of the CO2 gas is desirably 5%. The flow meter 520 controls an amount of the CO2 gas supplied from the CO2 Air tank 510 to the humidifier 410. The CO2 supply device 500 is connected to the cell culture chamber 100 through the humidifier 410 and the culture medium buffer 420. The CO2 gas of the CO2 Air tank 510 has a suitable humidity through the humidifier 410, and is supplied to the culture medium buffer 420. The concentration of CO2 of air inside the culture medium buffer 420 to which the CO2 gas having a suitable humidity is supplied is controlled. This air inside the culture medium buffer 420 of which the concentration of CO2 is controlled is supplied to the inside of the cell culture chamber 100. Since the CO2 gas is supplied to the cell culture chamber 100 by the CO2 supply device 500 successively, the CO2 concentration of the inner side of the cell culture chamber 100 can be maintained constantly.

The control space in which the ultrasound stimulation is controlled is formed in the cell culture chamber 100. The control space is composed of a focused zone A to which the ultrasound stimulation is excited and an unfocused zone B to which the ultrasound stimulation is not excited. Also, first sensor 110a, 110b is located in the focused zone A, and second sensor 111a, 111b is located in the unfocused zone B. the first sensor 110a, 110b and the second sensor 111a, 111b sense a sound pressure level of the focused zone A and the unfocused zone B respectively.

The controller 300 is connected to the plurality of the exciters 200a to 200j. An exciting signals $q_a$ to $q_j$ are inputted from a plurality of the signal generators (not figured) to the controller 300. Also, the controller 300 is connected to the first sensor 110a, 110b and the second sensor 111a, 111b, and the sound pressure levels of the focused zone A and the unfocused zone B sensed by the first sensor 110a, 110b and the second sensor 111a, 111b are inputted to the controller 300.

The controller 300 measures a transfer function related to the exciting signal $q_a$ to $q_j$ inputted to the plurality of the exciters 200a to 200j and the sound pressure signal $p_a$ to $p_j$ sensed by the plurality of the exciters 110a, 110b, 111a, 111b, and determines a controlled exciting signal for making the control brightness of Equation 11 maximized (control brightness control α) or making the control contrast 1 of Equation 13 maximized (control contrast 1 control β) or making the control contrast 2 of Equation 15 maximized (control contrast 2 control γ). The controller 300 transfers the determined controlled exciting signals to the plurality of the exciters 200a to 200j. Thus, the ultrasound mapping which excites a desired position of the inside of the cell culture chamber 100 with a desired type of an ultrasound field is performed.

As showed in FIG. 3, according to the apparatus for stimulating cell of the present invention, the outer chamber 10 surrounds the cell culture chamber 100, and the upper transparent substrate 130a and the lower transparent substrate 130b are located respectively in the upper side and the lower side of the cell culture chamber 100. Also, an Al upper substrate 120 and Al lower substrate 140 are installed to be separable in the upper side of the upper transparent substrate 130a and in the lower side of the lower transparent substrate 130b respectively. Since this Al upper substrate 120 and Al lower substrate 140 are separated, a fumigation for culturing the cell can be performed by a device as like an autoclave.

The exciter 200 is installed on the inner wall of the outer chamber 10. The impedance matching fluid 250 is filled between the exciter 200, the inner wall of the outer chamber 10 on which the exciter 200 is not installed and the cell culture chamber 100. Also, an Al upper substrate 131 is installed in the upper side of the cell culture chamber 100 through the fastening device 132 as like a bolt.

The upper transparent substrate 130a and the lower transparent substrate 130b are fastened to an upper plate and lower plate of the cell culture chamber 100 by the fastening device 132, 134 as like a bolt and fixed on an upper plate and lower plate of the cell culture chamber 100.

Figure 4:
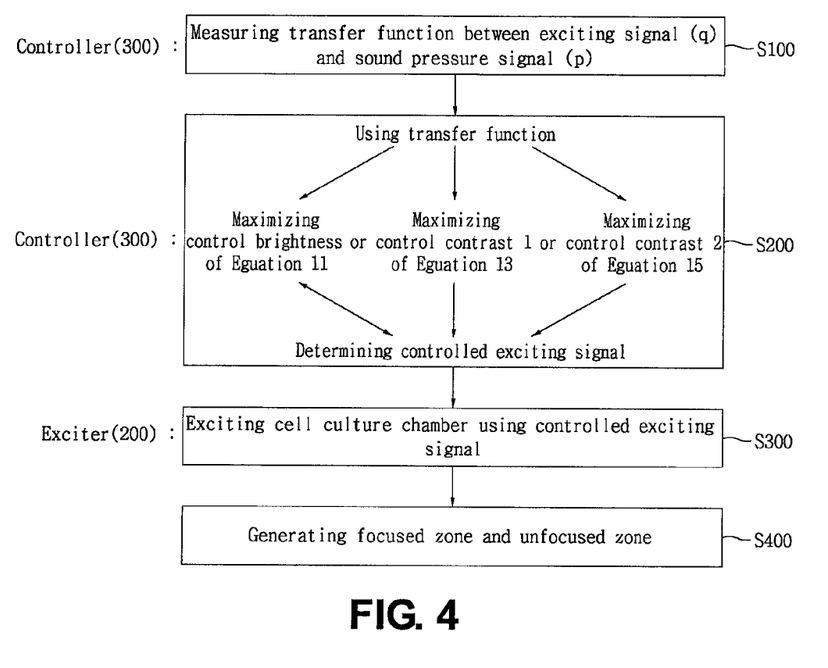
FIG. 4 is a flowchart illustrating the process of generating focused zone and unfocused zone within control space by using an apparatus for stimulating cell according to an embodiment of the present invention.

The process of generating focused zone and unfocused zone within control space by using the apparatus for stimulating cell of the present invention is described referring to FIG. 4. FIG. 4 is a flowchart illustrating the process of generating focused zone and unfocused zone within control space by using the apparatus for stimulating cell of the present invention.

Firstly, the controller measures the transfer function between the exciting signal and the sound pressure signal (Step S100). In the measurement of the transfer function, a lot of measurements are necessary according to the number of the ultrasound exciters and the ultrasonic sensors. So, the transfer function can be easily measured by a simple method which is used generally. The simple method is to measure the transfer function between the exciting signal and the sound pressure signal with only one measurement by inputting white noise to the plurality of exciters and identifying the contribution of each exciting source to the sound pressure signal sensed by each microphone.

And then, the controller determines the controlled exciting signals for maximizing the control brightness $\alpha$ of Equation 11 or maximizing the control contrast 1 $\beta$ of Equation 13 or maximizing the control contrast 2 $\gamma$ of Equation 15, and transmits the information about the controlled exciting signals to the ultrasound exciters (Step S200). The determined controlled exciting signal means as optimally exciting signals for generating the focused zone.

And then, the ultrasound exciter receives the optimally exciting signals for generating the focused zone from the controller and excites the cell culture chamber (Step S300). Accordingly, in the control space, the focused zone and the unfocused zone are generated (Step S400).

As described above, a technical composition of the present invention is to be understood that one skilled in the art is not to modify a technical idea or an essential feature of the present invention but to take effect as the other concrete embodiments.

Therefore, it is to be understood that embodiments described above are not qualifying but exemplary in all points. Also, the scope of the present invention will be included in the following claims than above detail explanation, and it is to be analyzed that the meaning and scope of the claims and all changes deducted from equivalent arrangements or modifications included within the scope of the present invention.

What is claimed is:

1. An apparatus for stimulating cell, comprising:
    a cell culture chamber configured to include cell and culture medium;
    a controller programmed to receive first and second exciting signals, to control magnitudes and phases of the received first and second exciting signals so that a sound pressure level in a focused zone is higher than a sound pressure level in a zone other than the focused zone and outputting first and second controlled exciting signals; and
    first, second, third, and fourth exciters configured to receive the first and second controlled exciting signals and to excite the cell culture chamber,
    the first, second, third, and fourth exciters arranged to surround the cell culture chamber,
    the controller being further programmed to control selectively the first, second, third, and fourth exciters to excite the cell culture chamber on the basis of where the focused zone is.

2. The apparatus as set forth in claim 1 further comprising:
    a transparent substrate located in the upper side and the lower side of the cell culture chamber.

3. The apparatus as set forth in claim 2 further comprising:
    an outer chamber configured to surround the cell culture chamber,
    wherein the first and second exciters are installed on the inner wall of the outer chamber.

4. The apparatus as set forth in claim 3,
    wherein an impedance matching fluid is filled in the outer chamber.

5. The apparatus as set forth in any one of claims 1 and 4 further comprising:
    a water bath configured to control a temperature of the culture medium, which is connected to the cell culture chamber,
    wherein the water bath includes a humidifier and a culture medium buffer connected between the humidifier and the cell culture chamber.

6. The apparatus as set forth in claim 5 further comprising:
    a CO2 supply device including an air tank and a flow meter, the follow meter being configured to control an amount of carbon dioxide ($CO_2$) gas concentration from air tank to the humidifier.

* * * * *